(12) United States Patent
Schlegel et al.

(10) Patent No.: US 8,394,849 B2
(45) Date of Patent: Mar. 12, 2013

(54) USE OF ARTEMISININ FOR TREATING TUMORS INDUCED BY ONCOGENIC VIRUSES AND FOR TREATING VIRAL INFECTIONS

(75) Inventors: Richard Schlegel, Rockville, MD (US); Dan-Paul Hartmann, Bethesda, MD (US); Astrid Baege, McLean, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 13/179,978

(22) Filed: Jul. 11, 2011

(65) Prior Publication Data

US 2012/0010278 A1    Jan. 12, 2012

Related U.S. Application Data

(62) Division of application No. 10/545,356, filed as application No. PCT/US2004/004067 on Feb. 12, 2004, now Pat. No. 7,989,491.

(60) Provisional application No. 60/446,743, filed on Feb. 12, 2003.

(51) Int. Cl.
*A61K 31/357* (2006.01)
(52) U.S. Cl. ........................................ 514/450
(58) Field of Classification Search .................. 514/450
See application file for complete search history.

(56) References Cited

U.S. PATENT DOCUMENTS

| 4,978,676 | A | 12/1990 | Thornfeldt |
| 5,219,880 | A | 6/1993 | Thornfeldt |
| 5,225,554 | A | 7/1993 | Avery et al. |
| 5,409,938 | A | 4/1995 | Boyd et al. |
| 5,578,637 | A | 11/1996 | Lai et al. |
| 5,639,761 | A | 6/1997 | Francois et al. |
| 5,677,468 | A | 10/1997 | Zheng et al. |
| 5,856,351 | A | 1/1999 | Zheng et al. |
| 6,160,004 | A | 12/2000 | Posner et al. |
| 6,297,272 | B1 | 10/2001 | Posner et al. |
| 2002/0169140 | A1 | 11/2002 | Prendergast |
| 2004/0115651 | A1 | 6/2004 | Bennett et al. |

FOREIGN PATENT DOCUMENTS

| EP | 0428773 A1 | 5/1991 |
| EP | 0713877 A1 | 5/1996 |
| WO | 01/42467 A2 | 6/2001 |
| WO | 01/49242 A2 | 7/2001 |
| WO | 02/24207 A1 | 3/2002 |
| WO | WO 03103588 A2 * | 12/2003 |
| WO | 2004-041176 A2 | 5/2004 |

OTHER PUBLICATIONS

Effereth et al.; "mRNA expression profiled for the response of human tumor cell lines to the antimalarial drugs artesunate, arteether, and artemether"; 2002; Biochemical Pharmacology; 64: 617-623.*

Schuller et al.; "Multimodal Intensification Therapy for Previously Untreated Advanced Resectable Squamous Cell Carcinoma of the Oral Cavity, Oropharynx, of Hypopharynx"; 2002; Cancer; 94: 3169-78.*

Lindel et al.; "Human papillomavirus positive squamous cell carcinoma of the oropharynx: a radiosensitive subgroup of head and neck carcinoma"; 2001; Cancer; 92(4): 804-13; PubMed abstract: PMID: 11550151.*

(Continued)

*Primary Examiner* — Timothy Thomas
(74) *Attorney, Agent, or Firm* — Morgan, Lewis & Bockius LLP

(57) ABSTRACT

In certain aspects, the invention relates to methods of treating proliferative oropharyngeal cancer, laryngeal cancer and esophageal cancer by administering artemisinin-related compounds.

8 Claims, 5 Drawing Sheets

Artemisinin

Dihydroartemisinin

OTHER PUBLICATIONS

Abramson et al., (2004) Latent human papillomavirus infection is comparable in the larynx and trachea, J. Med. Virol. (2004) 72:473-477.

Beekman et al., Stability of artemisinin in aqueous environments: impact on its cytotoxic action to Ehrlich ascites tumour cells, J. Pharm. Pharmacol. (1997) 49:1254-1258.

Bernard, The clinical importance of nomenclature, evolution and taxonomy of human papillomaviruses, J. Virol. (2005) 32S:S1-S6.

Besko et al., Susceptibility locus for epidermodysplaisa verruciformis not linked to cervical cancer in situ, Hereditas (2001) 135:61-63.

Chen et al., Inhibition of human cancer cell line growth and human umbilical vein endothelial cell angiogenesis by artemisinin derivatives in vitro, Pharmacol. Res. (2003) 48:231-236.

de Clerq, Molecular targets for antiviral agents, J. Pharmacol. Exp. Ther. (2001) 297:1-10.

de Villiers et al., Classification of papillomaviruses, Virol. (2004) 324-17-27.

Disbrow et al., Dihydroartemisinin is cytotoxic to papillomavirus-expression epithelial cells in vitro and in vivo, Cancer Res. (2005) 65:10854-10861.

Efferth et al., Antiviral activity of artesunate towards wild-type, recombinant and ganciclovir-resistant human cytomegaloviruses, J. Mol. Med. (2002) 80:233-242.

Efferth et al., The anti-malarial artesunate is also active against cancer, Int. J. Oncol., (2001) 18:767-773.

Favre et al., Psoriasis: a possible reservoir for human papillomavirus type 5, the virus associated with skin carcinomas of epidermodysplasia verruciformis, J. Invest. Dermatol. (1998) 110:311-317.

Garland, Human papillomavirus update with a particular focus on cervical disease, Pathology (2002) 34:213-224.

Gillison et al., Chapter 9: Role of mucosal human papillomavirus in nongenital cancers, J. Natl. Cancer Inst. Monogr. (2003) 31:57-65.

Haig et al., Immunity and counter-immunity during infection with the parapoxvirus orf virus, Virus Res. (2002) 88:3-16.

Hardwood et al., Detection of human papillomavirus DNA in PUVA-associated non-melanoma skin cancers, J. Invest. Dermatol. (1998) 111:123-127.

Klayman, An antimalarial drug from China, Science (1985) 228:1049-1055.

Kreimer et al., Human papillomavirus types in head and neck squamous cell carcinomas worldwide: a systematic review, Cancer Epidemiol. Biomarkers Prev. (2005) 14:467-475.

Long et al., Prevention, diagnosis, and treatment of cervical cancer, Mayo Clin. Proc. (2007) 82:1566-1574.

Longworth et al., Pathogenesis of human papillomaviruses in differentiating epithelia, Microbiol. Mol. Biol. Rev. (2004) 68:362-372.

Majewski et al., Do epidermodysplasia verruciformis human papillomaviruses contribute to malignant and benign epidermal proliferations? Arch. Dermatol. (2002) 138:649-654.

Moore et al., Oral administration of dihydroartemisinin and ferrous sulfate retarded implanted fibrosarcoma growth in the rat, Cancer Lett. (1995) 98:83-87.

Munoz et al., Epidemiologic classification of human papillomavirus types associated with cervical cancer, N. Engl. J. Med. (2003) 348:518-527.

Opsenica et al., Cholic acid derivatives as 1,2,4,5-tetraoxane carriers: structure and antimalarial and antiproliferative activity, J. Med. Chem, (2000) 43:3274-3282.

Posner et al., Antimalarial, anti-proliferative, and anti-tumor activities of artemisinin-derived, chemically robust, trioxane dimers, J. Med. Chem, (1999) 42:4275-4280.

Prignano et al., Prevalence of human papillomavirus type 5 DNA in lesional and non-lesional skin scales of Italian plaque-type psoriatic patients: association with disease severity, Clin. Microbiol. Infect. (2005) 11:47-51.

Rust et al., Human papillomavirus in cutaneous squamous cell carcinoma and cervix of patient with psoriasis and extensive ultraviolet radiation exposure, J. Am. Acad. Dermatol. (2001) 44:681-686.

Schon et al., Psoriasis, N. Engl. J. Med. (2005) 352:1899-1912.

Signgh et al., Selective toxicity of dihydroartemisinin and holotransferrin toward human breast cancer cells, Life Sci. (2001) 70:49-56.

Simon et al., Differential toxicities of anticancer agents among DNA repair and checkpoint mutants of *Saccharomyces cerevisiae*, Cancer Res. (2000) 60:328-333.

Sun et al., Antitumour activities of 4 derivatives of artemisic acid and artemisinin B in vitro, Zhonguo Yao Li Xue Bao (1992) 13:541-543.

Wolf et al., Increased prevalence of human papillomavirus in hairs plucked from patients with psoriasis treated with psoralen-UV-A, Arch. Dermatol. (2004) 140:317-324.

Zawadzka-Glos et al., Lower airway papillomatosis in children, Int. J. Pediatr. Otorhinolaryngol. (2003) 67:1117-1121.

Bren, Psoriasis: more than cosmetic, FDA Consumer Magazine, Sep.-Oct. 2004, http://www.fda.gov/fdac/features/2004/504_psoriasis.htmt.

Psoriasis and immune system involvement, National Psoriasis Foundation, http://www.psoriasis.org/research/known/immune.php, Updated Jun. 2004.

Psoriasis Health Center, 7 Psoriasis Triggers, edited by Cynthia Dennison-Haines, MC Sep. 1, 2005, http://www.webmd.com/skin-problems-and-treatments/psoriasis/7-psoriasis-triggers.

Medical Encyclopedia: *Molluscum contagiosum*, http://www.nlm.nih.gov/medlineplus/print/ency/article/000826.htm, (2009).

Fauquet et al., Virus Taxonomy, 8th Reports of the International Committee on Taxonomy of Viruses, Academic Press, Elsevier (May 27, 2005) p. 1162.

Database WPI Section Ch, Week 199730 Derwent Publications Ltd., London, GB; AN 1997-320247 XP002288323 & CN 1 105 238 A (Inst. Virology China Acad Preventive Medi) (Jul. 19, 1995).

Database WPI Section Ch. Week 199747 Derwent Publications Ltd., London, GB; AN 1997-503676 XP002288324 & CN 1 114 563 A (LI Z) (Jan. 10, 1996).

\* cited by examiner

USE OF ARTEMISININ FOR TREATING TUMORS INDUCED BY ONCOGENIC VIRUSES AND FOR TREATING VIRAL INFECTIONS

RELATED APPLICATIONS

This application is a Divisional Application of U.S. patent application Ser. No. 10/545,356 with a national stage commencement date of Aug. 11, 2005, now U. S. Pat. No. 7,989, 491 which is a U.S. National Phase Application of International Application PCT/US2004/004067, filed Feb. 12, 2004, which claims the benefit of U.S. Provisional Application 60/446,743, filed Feb. 12, 2003, all of which are hereby incorporated by reference in their entireties.

BACKGROUND

Despite the advent of the Papanicolaou (Pap) smear, cervical cancers and pre-cancers remain important health problems for women, especially in poorly monitored women in the United States and developing countries. Worldwide, 250,000 women die annually from this cancer. Cervical dysplasia is a premalignant or precancerous change to the cervical cells, and can progress into cervical cancer without treatment.

The major risk factor for cervical cancer is infection by human papillomavirus (HPV). Papillomavirus infections are responsible for 99% of cervical cancers in women, as well as the majority of anorectal squamous cell carcinomas. In addition, papillomaviruses are found in squamous and basal cell carcinomas of the skin as well as in squamous carcinoma cells of the mouth, oropharynx, and larynx. The papillomaviruses also induce many benign tumors including genital warts and common warts of the hands and feet. They also induce laryngeal papillomas of children and adults. Currently, there are no pharmaceutical therapies available for the treatment of human papillomavirus (HPV) infections and the accompanying tumors that they induce.

Clinical trials have evaluated the injection of interferon into papillomavirus lesions and have shown some effect. However, the viral infections recur immediately after withdrawal of the interferon. Topical applications of other compounds such as 5-fluorouracil (5FU) and podophyllotoxin are toxic and kill both infected and normal cells. These treatments are not highly effective and do not specifically target the tumor cells. A recent therapy which is in trials is the use of Ionic Contra Viral Therapy (ICVT), which was developed by Henderson Marley (see, e.g., WO 01/49300, WO 01/49242, WO 01/66100, WO 02/24207). Since antiviral therapies are not available for papillomavirus infections, the current clinical approach is to develop a vaccine that will prevent infection. Vaccines offer great promise and animal studies have found them to be highly protective. However, among the 100 types of papillomaviruses that infect humans, there are at least 5 types that induce cervical cancer and it will be necessary to develop a multivalent vaccine in order to prevent this cancer in women. Current trials are evaluating only a monovalent vaccine against HPV type 16 and these trials will not be completed for several years. It will then be necessary to develop techniques to express the capsid proteins of the other HPV types, which is not necessarily a routine procedure.

For many years, virus diseases have been considered as intractable to selective antiviral chemotherapy because the replicative cycle of the virus was assumed to be too closely interwoven with normal cell metabolism and any attempt to suppress virus reproduction would also kill (or severely harm) uninfected cells as well. Clearly, there is a need for additional approaches to treating conditions such as virus infections and cancers (e.g., cervical cancer) resulting from virus infection, which are significant public health problem.

SUMMARY OF THE INVENTION

The present invention relates to methods of treating infection caused by viruses including human papillomavirus (HPV), human T-lymphotropic virus type I (HTLV-1), herpes virus (e.g., Epstein-Barr virus (EBV), cytomegalovirus (CMV)), SV40-like virus, hepatitis virus, human immunodeficiency virus (HIV), adenovirus, and influenza virus, as well as treatment of cervical disorders associated with virus infection (e.g., cervical cancer and cervical dysplasia), through the administration of artemisinin and/or artemisinin derivatives. The present invention particularly relates to methods of selectively killing or inhibiting growth of cells, such as premalignant (precancerous) and malignant (cancerous) cells by administering artemisinin and/or an artemisinin derivative (one or more derivatives).

In one embodiment, the invention provides a method of treating an individual suffering from a virus infection. An individual (patient or subject) suffering from a virus infection is treated by administering to the individual a therapeutically effective amount of an artemisinin-related compound. As used throughout the application, the term "artemisinin-related compound" includes both artemisinin and artemisinin derivatives (analogs). The viral infection may be caused by a virus such as human papillomavirus (HPV), human T-lymphotropic virus type I (HTLV-1), herpes virus (e.g., Epstein-Barr virus (EBV), cytomegalovirus (CMV)), SV40-like virus, hepatitis virus, human immunodeficiency virus (HIV), adenovirus, and influenza virus.

The method of the present invention can be used to treat both premalignant and malignant cervical lesions due to papillomavirus. In another embodiment, the invention provides a method of treating an individual suffering from a proliferative cervical disorder. In this embodiment, an individual suffering from a proliferative cervical disorder is treated by administering to the individual a therapeutically effective amount of an artemisinin-related compound. As used herein, the term "proliferative cervical disorder" includes cervical cancer and cervical precancer (e.g., cervical dysplasia). The proliferative cervical disorder may be associated with papillomavirus infection.

Artemisinin derivatives include, but are not limited to, dihydroartemisinin, artemether, arteether, artesunate, artelinic acid, and dihydroartemisinin propyl carbonate. An artemisinin-related compound may be administered to the individual by a variety of routes, for example, orally, topically, parenterally, intravaginally, systemically, intramuscularly, rectally or intravenously. In certain embodiments, an artemisinin-related compound is formulated with a pharmaceutical carrier.

In some embodiments, artemisinin or an artemisinin derivative is combined with other anti-viral or anti-cancer therapies, such as administration of an anti-viral or anti-cancer agent, radiation therapy, phototherapy or immunotherapy. The anti-viral or anti-cancer agent can be administered with an artemisinin-related compound either in the same formulation or in separate formulations, to enhance treatment. In these embodiments, the artemisinin-related compound and the other therapies can be administered at the same time (simultaneously) or at separate times (sequentially), provided that they are administered in such a manner and sufficiently close in time to have the desired effect.

In another embodiment, the invention provides a method of killing or inhibiting growth of cells that are infected by human papillomavirus, such as cervical cancer cells, anorectal squamous cancer cells, squamous carcinoma cells of the skin, basal carcinoma cells of the skin, and squamous carcinoma cells of the mouth, oropharynx, and larynx. Squamous cell carcinomas of the head and neck, esophagus, trachea, and bronchi (some of which contain HPV) are also potential targets. The infected cells are contacted with an artemisinin-related compound in a sufficient amount to kill or inhibit growth of infected cells. In this embodiment, a therapeutically effective amount of an artemisinin-related compound is administered to an individual in need of treatment, e.g., for treatment of cervical cancer, anorectal cancer, squamous or basal cell skin cancer, and squamous carcinoma of the mouth, oropharynx, and larynx. The artemisinin-related compound is administered by a route appropriate for its delivery to the site(s) at which treatment is needed (e.g., topically, intravaginally, rectally, orally, systemically, intramuscularly or intravenously) in an amount sufficient to kill or inhibit growth of cells infected by human papillomavirus.

In another embodiment, the invention provides a method of killing or inhibiting growth of cells that are infected by oncogenic viruses such as HPV, HTLV-1, herpes virus (e.g., EBV or CMV), SV40-like viruses, hepatitis virus, or adenovirus. In addition, HIV, and influenza virus are potential targets. The infected cells are contacted with an artemisinin-related compound in a sufficient amount to kill or inhibit growth of the infected cell. In this embodiment, a therapeutically effective amount of an artemisinin-related compound is administered to an individual in need of treatment of infection by HPV, HTLV-1, herpes virus (e.g., EBV or CMV), SV40-like virus, hepatitis virus, HIV, adenovirus or influenza virus, by a route which results in (is appropriate for) delivery of an amount sufficient to kill or inhibit growth of infected cells to the sites at which treatment is needed.

In another embodiment, the invention provides a method of treating an individual infected with human papillomavirus (HPV). In this embodiment, a therapeutically effective amount of an artemisinin-related compound is administered to the individual by a route appropriate for delivery of an amount sufficient to kill or inhibit growth of infected cells to the site(s) at which treatment is needed. This embodiment is useful to treat a variety of conditions in which an individual is infected with HPV, such as conditions in which the cells to be killed or inhibited are cervical cancer cells, anorectal squamous cancer cells, squamous carcinoma cells of the skin, basal carcinoma cells of the skin, and squamous carcinoma cells of the mouth, oropharynx, and larynx. Squamous cell carcinomas of the head and neck, esophagus, trachea, and bronchi are also potential targets In another embodiment, the invention provides a method of treating an individual infected with a virus such as HPV, HTLV-1, herpes virus (e.g., EBV or CMV), SV40-like virus, hepatitis virus, HIV, adenovirus or influenza virus. In this embodiment, a therapeutically effective amount of an artemisinin-related compound is administered to an individual in need of treatment of infection by HPV, HTLV-1, herpes virus (e.g., EBV or CMV), SV40-like virus, hepatitis virus, HIV, adenovirus or influenza virus, by a route which results in (is appropriate for) delivery of an amount sufficient to kill or inhibit growth of infected cells to the sites at which treatment is needed.

In another embodiment, the invention provides a method of treating a condition caused by human papillomavirus in an individual. In this embodiment, a therapeutically effective amount of an artemisinin-related compound is administered to the individual by a route appropriate for delivery of an amount sufficient to kill or inhibit growth of infected cells to the site(s) at which treatment is needed. Conditions caused by HPV that may be treated by the subject methods include, but are not limited to, cervical cancer, anorectal squamous cancer, squamous carcinoma or basal carcinoma of the skin, and squamous carcinoma of the mouth, oropharynx, larynx, head and neck, esophagus, trachea, and bronchi.

In another embodiment, the invention provides a method of treating a condition caused by a virus in an individual. Conditions caused by a virus, such as HPV, HTLV-1, herpes virus (e.g., EBV or CMV), SV40-like virus, hepatitis virus, HIV, adenovirus, or influenza virus, can be treated by the method of the present invention. In this embodiment, a therapeutically effective amount of an artemisinin-related compound is administered to the individual by a route appropriate for delivery of an amount sufficient to kill or inhibit growth of infected cells to the site(s) at which treatment is needed. Conditions caused by such viruses that may be treated by the subject methods include, but are not limited to, cancers, such as cervical cancer, anorectal squamous cancer, squamous carcinoma or basal carcinoma of the skin, and squamous carcinoma of the mouth, oropharynx, larynx. Viruses which have the ability to induce tumors in man or animals are referred to as "oncogenic" viruses. That is, they target oncogenic viruses. They include, but are not limited to, HPV, HTLV-1, herpes virus (e.g., EBV or CMV), SV40-like virus, hepatitis virus, and adenovirus. Artemisinin-related compounds can also be used to inhibit non-oncogenic viruses, such as HIV and influenza virus.

In another embodiment, the invention provides a method of treating non-malignant papillomavirus infections, such as benign tumors in an individual, e.g., laryngeal papillomas, genital papillomas (warts), and common warts of hands and feet. The infected cells are contacted with an artemisinin-related compound in an amount sufficient to kill or inhibit growth of the cells. For example, a therapeutically effective amount of an artemisinim-related compound is administered to an individual by a route which results in delivery of the compound to target site(s) (e.g., laryngeal tissue, genital warts or common warts of hands and feet) at which infected cells are to be killed or inhibited.

In another embodiment, the invention provides a method of treating an individual suffering from a tumor induced by an oncogenic virus. In this embodiment, an individual suffering from a tumor which is induced by an oncogenic virus is administered a therapeutically effective amount of an artemisinin-related compound. Oncogenic viruses are a subset of viruses that include, but is not limited to, HPV, HTLV-1, herpes virus (e.g., EBV or CMV), SV40-like virus, hepatitis virus, and adenovirus. The oncogenic virus-induced tumors can be in humans or nonhuman animals. To illustrate, tumors induced by papillomavirus include lesions at the following sites: cervix, other genital sites (e.g., vagina, penis etc.), anal, oral, upper respiratory, and epidermal. Tumors induced by SV40-like virus include human mesotheliomas, osteosarcomas, and parotid gland tumors. Tumors induced by a herpes virus such as EBV, include nasopharyngeal carcinomas and Hodgkins disease. Tumors induced by HTLV-1 include lymphomas. Tumors induced by hepatitis virus include hepatocellular carcinomas.

In another embodiment, the invention provides a method of killing or inhibiting a squamous cell carcinoma in an individual, comprising administering to the individual a therapeutically effective amount of an artemisinin-related compound. The squamous cell carcinoma is selected from the group consisting of squamous cell carcinomas of head and neck, oral, oropharyngeal, laryngeal, tracheal, and bronchial. Optionally, the squamous cell carcinoma contains HPV infection.

In another embodiment, the invention provides a method of killing or inhibiting a squamous cell carcinoma, comprising contacting the carcinoma with an artemisinin-related compound in an amount sufficient to kill or inhibit growth of carcinoma cells.

In another embodiment, the invention provides a method of inhibiting replication of a virus in an individual, comprising administering to the individual a therapeutically effective amount of an artemisinin-related compound. The virus is selected from the group consisting of: human papillomavirus (HPV), human T-lymphotropic virus type I (HTLV-1), herpes virus, SV40-like virus, hepatitis virus, human immunodeficiency virus (HIV), adenovirus, and influenza virus. In some aspects, the virus is an oncogenic virus (e.g., HPV, HTLV-1, herpes virus, SV40-like virus, hepatitis virus or adenovirus). In other aspects, the virus is an non-oncogenic virus (e.g., HIV or influenza virus).

In another embodiment, the invention provides a method of inhibiting replication of a virus, comprising contacting the virus with an artemisinin-related compound in an amount sufficient to inhibit replication of the virus.

In yet another embodiment, the invention provides a pharmaceutical composition comprising an artemisinin-related compound and a second therapeutic agent which is not an artemisinin-related compound. Preferably, the second therapeutic agent is a chemotherapeutic agent.

In all embodiments of methods of treating an individual, one or more artemisinin-related compounds can be administered together (simultaneously) or at different times (sequentially). In addition, artemesinin-related compounds can be administered with another type or types of compounds (non-artemisinin compounds). The two types of compounds may be administered simultaneously or sequentially.

DETAILED DESCRIPTION OF THE INVENTION

The present invention is based, in part, on Applicants' discovery that artemisinin and/or artemisinin derivatives (analogs) are effective in killing or inhibiting growth of cells that are transformed by human papillomavirus (e.g., cervical cancer cells) and cells that are transformed by other types of virus such as HTLV-1, herpes virus, SV40-like virus, hepatitis virus, HIV, adenovirus or influenza virus. As described herein, Applicants have shown that artemisinin kills cervical cancer cells, but not normal cervical cells. Therefore, artemisinin and its derivatives can be used to treat virus infections, and conditions caused by such virus infections, such as cervical cancers and cervical precancers. Artemisinin is currently used in humans as an antimalarial drug and can be administered both topically and systemically.

In certain embodiments, the invention provides methods of treating an individual suffering from either a virus infection or a proliferative cervical disorder. As used herein, the individual (patient or subject) to be treated by the subject methods can be either a human or a non-human animal. Such individual is treated by administering to the individual a therapeutically effective amount of an artemisinin-related compound. As used herein, the term "artemisinin-related compound" includes both artemisinin and artemisinin derivatives or analogs. The artemisinin derivatives or analogs may be synthetic, semisynthetic or natural.

In one aspect, the method of the present invention can be used to treat viral infection in an individual caused by human papillomavirus (HPV), human T-lymphotropic virus type I (HTLV-1), herpes virus (e.g., EBV or CMV), SV40-like virus, hepatitis virus, human immunodeficiency virus (HIV), adenovirus, or influenza virus. The present method can also be used to treat infections caused by other viruses that are responsive to treatment by artemisinin or artemisinin derivatives, such as DNA viruses and RNA viruses. Such virus may or may not cause cancer.

In another aspect, the present method is a method of treating a proliferative cervical disorder, such as cervical cancer and cervical precancer (e.g., cervical dysplasia), in an individual. As used herein, the term "proliferative cervical disorder" refers to any disease/disorder of the cervix characterized by unwanted or aberrant proliferation of cervical tissue. As one skilled in the art would understand, the proliferative cervical disorder may be associated with a virus infection such as papillomavirus infection.

In one embodiment, the invention provides a method of killing or inhibiting growth of cells that are infected by human papillomavirus, such as cervical cancer cells, anorectal squamous cancer cells, squamous carcinoma cells of the skin, basal carcinoma cells of the skin, and squamous carcinoma cells of the mouth, oropharynx, larynx, head and neck, esophagus, trachea, and bronchi. The infected cells are contacted with an artemisinin-related compound in a sufficient amount to kill or inhibit growth of infected cells. In this embodiment, a therapeutically effective amount of an artemisinin-related compound is administered to an individual in need of treatment, e.g., for treatment of cervical cancer, anorectal cancer, squamous carcinoma or basal carcinoma of the skin, and squamous carcinoma of the mouth, oropharynx, larynx, head and neck, esophagus, trachea, and bronchi. The artemisinin-related compound is administered by a route appropriate for its delivery to the site(s) at which treatment is needed (e.g., topically, intravaginally, rectally, orally, systemically, intramuscularly or intravenously) in an amount sufficient to kill or inhibit growth of cells infected by human papillomavirus.

In another embodiment, the invention provides a method of killing or inhibiting growth of cells that are infected by a virus such as HPV, HTLV-1, herpes virus (e.g., EBV or CMV), SV40-like virus, hepatitis virus, HIV, adenovirus or influenza virus. The infected cells are contacted with an artemisinin-related compound in a sufficient amount to kill or inhibit growth of the infected cell. In this embodiment, a therapeutically effective amount of an artemisinin-related compound is administered to an individual in need of treatment of infection by HPV, HTLV-1, herpes virus (e.g., EBV or CMV), SV40-like virus, hepatitis virus, HIV, adenovirus or influenza virus, by a route which results in (is appropriate for) delivery of an amount sufficient to kill or inhibit growth of infected cells to the sites at which treatment is needed.

In one embodiment, the invention provides a method of treating an individual infected with human papillomavirus (HPV). In this embodiment, a therapeutically effective amount of an artemisinin-related compound is administered to the individual by a route appropriate for delivery of an amount sufficient to kill or inhibit growth of infected cells to the site(s) at which treatment is needed. This embodiment is useful to treat a variety of conditions in which an individual is infected with HPV, such as conditions in which the cells to be killed or inhibited are cervical cancer cells, anorectal squamous cancer cells, squamous carcinoma cells or basal carcinoma cells of the skin, and squamous carcinoma cells of the mouth, oropharynx, and larynx, or in some squamous cell carcinomas of the head and neck, esophagus, trachea, and bronchi.

In another embodiment, the invention provides a method of treating an individual infected with a virus, such as HPV, HTLV-1, herpes virus (e.g., EBV or CMV), SV40-like virus, hepatitis virus, HIV, adenovirus or influenza virus. In this embodiment, a therapeutically effective amount of an artemisinin-related compound is administered to an individual in need of treatment of infection by HPV, HTLV-1, herpes virus (e.g., EBV or CMV), SV40-like virus, hepatitis virus, HIV, adenovirus or influenza virus, by a route which results in (is appropriate for) delivery of an amount sufficient to kill or inhibit growth of infected cells to the sites at which treatment is needed.

In one embodiment, the invention provides a method of treating a condition caused by human papillomavirus in an individual. In this embodiment, a therapeutically effective amount of an artemisinin-related compound is administered to the individual by a route appropriate for delivery of an amount sufficient to kill or inhibit growth of infected cells to the site(s) at which treatment is needed. Conditions caused by HPV that may be treated by the subject methods include, but are not limited to, cervical cancer, anorectal squamous cancer, squamous carcinoma or basal carcinoma of the skin, and squamous carcinoma of the mouth, oropharynx, larynx, head and neck, esophagus, trachea, and bronchi.

In another embodiment, the invention provides a method of treating a condition caused by a virus in an individual. The virus includes HPV, HTLV-1, herpes virus (e.g., EBV or CMV), SV40-like virus, hepatitis virus, HIV, adenovirus, and influenza virus. In this embodiment, a therapeutically effective amount of an artemisinin-related compound is administered to the individual by a route appropriate for delivery of an amount sufficient to kill or inhibit growth of infected cells to the site(s) at which treatment is needed. Conditions caused by such viruses that may be treated by the subject methods include, but are not limited to, cervical cancer, anorectal squamous cancer, squamous carcinoma or basal carcinoma of the skin, and squamous carcinoma of the mouth, oropharynx, and larynx. Squamous cell carcinomas of the head and neck, esophagus, trachea, and bronchi can also be treated in this manner.

In another embodiment, the invention provides a method of treating non-malignant papillomavirus infections, such as benign tumors in an individual, e.g., laryngeal papillomas, genital papillomas (warts), and common warts of hands and feet. The infected cells are contacted with an artemisinin-related compound in an amount sufficient to kill or inhibit growth of the cells. For example, a therapeutically effective amount of an artemisinim-related compound is administered to an individual by a route which results in delivery of the compound to target site(s) (e.g., laryngeal tissue, genital warts or common warts of hands and feet) at which infected cells are to be killed or inhibited.

In another embodiment, the invention provides a method of treating an individual suffering from a tumor induced by an oncogenic virus. In this embodiment, an individual suffering from a tumor which is induced by an oncogenic virus is administered a therapeutically effective amount of an artemisinin-related compound. Oncogenic viruses are a specific subset of viruses that include, but is not limited to, HPV, HTLV-1, herpes virus (e.g., EBV, CMV, HHV6, or HHV8), SV40-like virus, hepatitis virus, and adenovirus. The oncogenic virus-induced tumors can be in man or in animals. To illustrate, tumors induced by papillomavirus include lesions at the following sites: cervix, other genital sites (e.g., vagina, penis etc.), anal, oral, upper respiratory, and epidermal. Tumors induced by SV40-like virus include human mesotheliomas, osteosarcomas, and parotid gland tumors. Tumors induced by a herpes virus such as EBV, include nasopharyngeal carcinomas and Hodgkins disease. Tumors induced by another herpes virus such as herpes virus type 8 (HHV8), also referred to as KSV, include Kaposi's sarcoma. Kaposi's sarcoma is a malignant condition and is often diagnosed in immuno-suppressed patients infected with HIV. This tumor usually presents as a skin lesion. Tumors induced by HTLV-1 include lymphomas. Tumors induced by hepatitis virus include hepatocellular carcinomas.

In another embodiment, the invention provides a method of killing or inhibiting a squamous cell carcinoma in an individual, comprising administering to the individual a therapeutically effective amount of an artemisinin-related compound. The squamous cell carcinoma is selected from the group consisting of squamous cell carcinomas of head and neck, oral, oropharyngeal, laryngeal, tracheal, and bronchial. Optionally, the squamous cell carcinoma contains HPV infection.

In another embodiment, the invention provides a method of killing or inhibiting a squamous cell carcinoma, comprising contacting the carcinoma with an artemisinin-related compound in an amount sufficient to kill or inhibit growth of carcinoma cells.

In another embodiment, the invention provides a method of inhibiting the replication of a virus in an individual, comprising administering to the individual a therapeutically effective amount of an artemisinin-related compound. The virus is selected from the group consisting of: human papillomavirus (HPV), human T-lymphotropic virus type I (HTLV-1), herpes virus, SV40-like virus, hepatitis virus, human immunodeficiency virus (HIV), adenovirus, and influenza virus. In some aspects, the virus is an oncogenic virus (e.g., HPV, HTLV-1, herpes virus, SV40-like virus, hepatitis virus or adenovirus). In other aspects, the virus is an non-oncogenic virus (e.g., HIV or influenza virus).

In another embodiment, the invention provides a method of inhibiting the replication of a virus, comprising contacting the virus with an artemisinin-related compound in an amount sufficient to inhibit the replication of the virus.

In yet another embodiment, the invention provides a pharmaceutical composition comprising an artemisinin-related compound and a second therapeutic agent which is not an artemisinin-related compound. Preferably, the second therapeutic agent is a chemotherapeutic agent.

Artemisinin-Related Compound.

The term "artemisinin-related compound," as used herein, refers to both artemisinin and artemisinin derivatives or analogs. Artemisinin (Qinghaosu) is a naturally occurring substance, obtained by purification from sweet wormwood, *Artemisia annua*. L. Artemisinin and its analogs are sesquiterpene lactones with a peroxide bridge.

The subject methods contemplate the use of artemisinin derivatives or analogs. Analogs of artemisinin which have higher solubility in water are dihydroartemisinin, artemether, artesunate, arteether, propylcarbonate dihydroartemisinin, and artelinic acid.

The very low toxicity of these compounds to humans is a major benefit. Artesunate, for example, is twice as safe as artemether and only one-fiftieth as toxic as chloroquinine, the most common antimalarial drug.

Therapeutically Effective Amount of Artemisinin-Related Compounds

Methods of the present invention comprise administering a therapeutically effective amount of an artemisinin-related compound (one or more artemisinin-related compound). The phrase "therapeutically effective amount," as used herein, refers to an amount that results in death of cells infected by a virus, such as HPV, HTLV-1, herpes virus, SV40-like virus, hepatitis virus, HIV, adenovirus or influenza virus. For example, a therapeutically effective amount of an artemisinin-related compound kills or inhibits growth of cervical cancer cells; squamous and basal cell carcinomas of the skin; anorectal squamous cell carcinomsas; Kaposi's sarcoma, laryngeal papillomas and benign tumors, such as genital warts and warts of the hands and feet.

Artemisinin is a relatively safe drug and produces few side-effects, even at high doses. Oral doses of 70 mg/kg/day for 6 days have been used in humans for malaria treatment. Furthermore, more potent analogs of this and similar compounds are also available. Higher efficacy of artemisinin action can be achieved by other means. For example, artemisinin is more reactive with heme than with free iron (Hong et al., 1974, Mol. Biochem. Parasit., 63:121-128). Iron can be introduced into target cells using transferrin (see, e.g., Stout et al., 1992, Biochim. Biophy. Res. Comm., 189:765-770) or the heme-carrying compound hemoplexin (see, e.g., Smith et al., 1988, Biochem. J., 256:941-950; Smith et al., 1990, Europ. J. Cell Biol., 53:234-245). The concentrations of agents for enhancing intracellular iron concentrations in the practice of the present invention will generally range up to the maximally tolerated dose for a particular subject and agent, which will vary depending on the agent, subject, disease condition and other factors. Dosages ranging from about 1 to about 100 mg of iron per kilogram of subject body weight per day will generally be useful for this purpose.

The dose of artemisinin or artemisinin derivative compounds administered to an individual in need of treatment will vary and will be determined for each individual with reference to, for example, the compound used, the route of administration, and the physical condition and body size of the individual. To illustrate, about 0.1 to about 100 mg per kilogram of body weight per day can be administered. In further embodiments, from about 1 to about 90 mg per kilogram of body weight per day is administered. Alternatively, from about 1 to about 75 mg per kilogram of body weight per day can be administered. The daily dosage may be administered as a single dosage or may be divided into multiple doses.

Actual dosage levels of the artemisinin-related compound may be varied so as to obtain amounts at the site of target cells (e.g., virus infected cells or abnormal cervical cells), effective to obtain the desired therapeutic or prophylactic response. Accordingly, the selected dosage level will depend on the nature and site of the target cells, the desired quantity of artemisinin-related compound required at the target cells for inhibition or killing, the nature of the artemisinin-related compound employed, the route of administration, and other factors. Topical or oral administration, for instance, may typically be carried out one or more times a day, such as one to three times daily.

Pharmaceutical Compositions.

In certain embodiments of methods of the present invention, artemisinin-related compounds are formulated with a pharmaceutically acceptable carrier.

Artemisinin or an artemisinin derivative can be administered alone or as a component of a pharmaceutical formulation (composition). The compounds may be formulated for administration in any convenient way for use in human or veterinary medicine. In certain embodiments, the compound included in the pharmaceutical preparation may itself be active, or may be a prodrug. The term "prodrug" refers to compounds which, under physiological conditions, are converted into therapeutically active agents.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the artemisinin-related compounds include those suitable for oral/nasal, topical, parenteral, intravaginal and/or rectal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these formulations or compositions include combining an artemisinin-related compound and a carrier and, optionally, one or more accessory ingredients. In general, the formulations are prepared by combining an artemisinin-related compound with a liquid carrier, or a finely divided solid carrier, or both, and then, if necessary, shaping the product.

Formulations of the artemisinin-related compounds suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an artemisinin-related compound as an active ingredient. An artemisinin-related compound may also be administered as a bolus, electuary or paste.

In solid dosage forms for oral administration (capsules, tablets, pills, dragees, powders, granules, and the like), an artemisinin-related compound is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the artemisinin-related compounds include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the invention can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration of an artemisinin-related compound include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to an artemisinin-related compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an artemisinin-related compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more artemisinin-related compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of the artemisinin-related compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations of the artemisinin-related compounds for intravaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Optionally, such formulations suitable for vaginal administration also include pessaries, tampons, creams, gels, pastes, foams or spray formulations containing such carriers as are known in the art to be appropriate.

In another embodiment, artemisinin or artemisinin derivative compounds can be administered to animals in animal feed. For example, these compounds can be included in an appropriate feed premix, which is then incorporated into the complete ration in a quantity sufficient to provide a therapeutically effective amount to the animal. Alternatively, an intermediate concentrate or feed supplement containing the artemisinin-related compounds can be blended into the feed. The way in which such feed premixes and complete rations can be prepared and administered are described in reference books (see, e.g., "Applied Animal Nutrition," W.H. Freedman and CO., San Francisco, U.S.A., 1969 or "Livestock Feeds and Feeding," O and B books, Corvallis, Ore., U.S.A., 1977).

Methods of Administration.

In certain embodiments, the subject methods of the invention can be used alone. Alternatively, the subject methods may be used in combination with other anti-viral or anti-cancer therapeutic approaches (e.g., administration of an anti-viral or anti-cancer agent, radiation therapy, phototherapy or immunotherapy) directed to treatment or prevention of proliferative cervical disorders or virus infections. For example, such methods can be used in prophylactic cancer prevention, prevention of cancer recurrence and metastases after surgery, and as an adjuvant of other traditional cancer therapy. Similarly, the subject methods of the invention may be combined with other antiviral therapies.

Thus, the subject methods of the invention may further include as optional ingredients one or more agents already known for their use in the inhibition of cervical cancer or precancer cells, for added clinical efficacy. These agents include, but are not limited to, interleukin-2,5'-fluorouracil, nedaplatin, methotrexate, vinblastine, doxorubicin, carboplatin, paclitaxel (Taxol), cisplatin, 13-cis retinoic acid, pyrazoloacridine, and vinorelbine. Appropriate amounts in each case will vary with the particular agent, and will be either readily known to those skilled in the art or readily determinable by routine experimentation. methotrexate, vinblastine, doxorubicin, and cisplatin.

In other cases, the subject methods of the invention may further include as optional ingredients one or more agents already known for their anti-viral effects, for added clinical efficacy. These agents include, but are not limited to, 5'-fluorouracil, interferon alpha, imiquimod, lamivudine, arsenic trioxide, capsaicin, nucleoside analogues (e.g., acyclovir), and antiviral vaccines.

The artemisinin-related compounds may be employed in vitro, in vivo or ex vivo for killing or inhibition of affected cells. For in vivo applications, artemisinin-related compounds can be administered to a human or other animal subject, together with a pharmaceutically acceptable carrier, to localize a sufficient amount at target tissue sites to facilitate killing or inhibition of target cells.

EXEMPLIFICATION

The invention now being generally described, it will be more readily understood by reference to the following examples, which are included merely for purposes of illustration of certain aspects and embodiments of the present invention, and are not intended to limit the invention.

Example 1

Effect of Artemisinin and its Analogs on Cervical Cancer Cells

Figure 1:
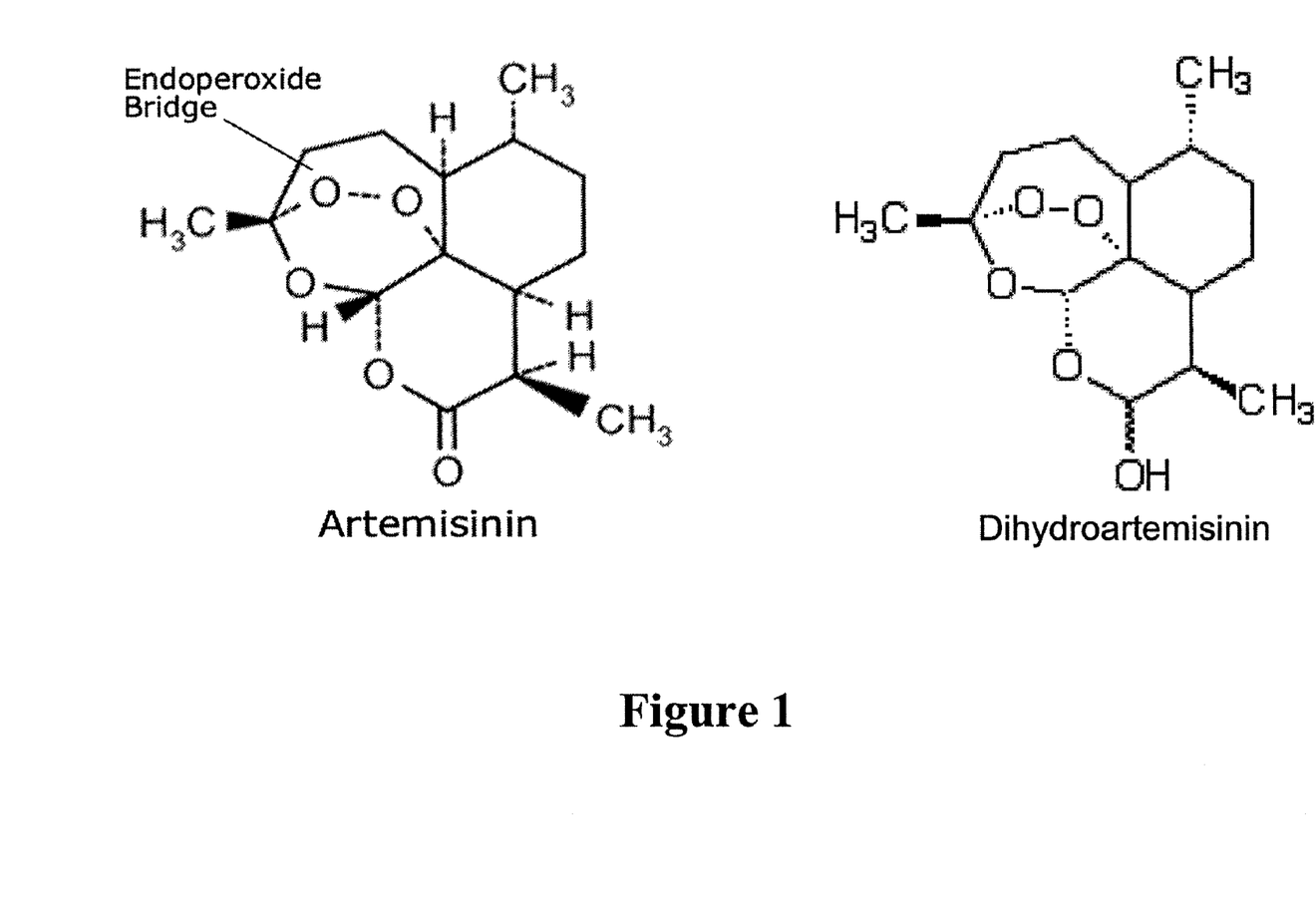
FIG. 1 shows structures of artemisinin and its biologically active metabolic derivative, dihydroartemisinin (DHA).
Figure 2:
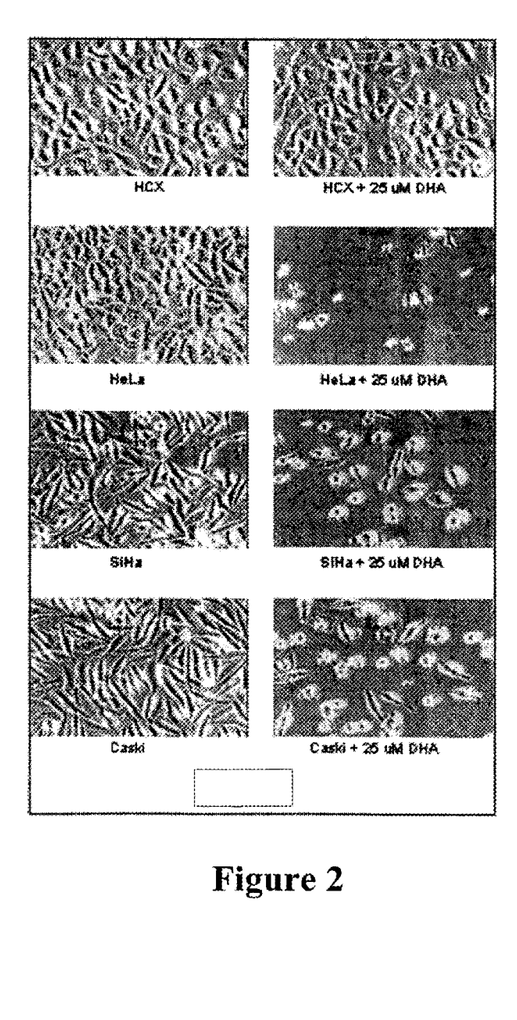
FIG. 2 shows that artemisinin is lethal for cervical cancer cells.

FIG. 2 shows that artemisinin is lethal for cervical cancer cells. The indicated cervical cancer cell lines were treated with 25 µM artemisinin (or control solvent) for 3 days and then photographed with a phase contrast microscope. Normal cervical cells (HCX) showed little change in morphology in response to artemisinin whereas the cervical cancer cells rounded up and detached from the tissue culture plate.

Figure 3:
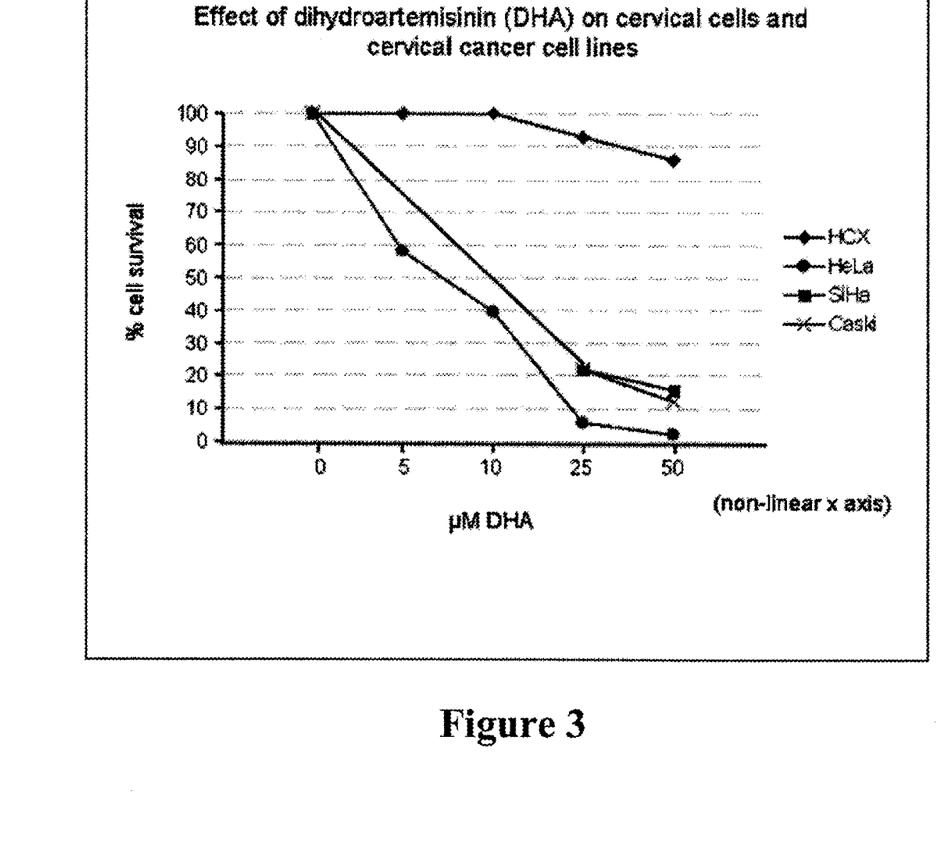
FIG. 3 shows that cervical cancer cells, but not normal cervical cells, are efficiently killed by artemisinin.

FIG. 3 shows that cervical cancer cells, but not normal cervical cells, are efficiently killed by artemisinin A dose-response curve is shown for the effects of dihydroartemisinin (DHA) on the viability of normal cervical cells (HCX) and 3 cervical cancer cell lines (HeLa, SiHa, Caski) The cervical cancer cell lines demonstrated 80% loss of viability within 3 days of treatment with 25 µM DHA. HeLa cells were the most sensitive, exhibiting 95% cell death at 25 µM DHA.

Example 2

Effect of Dihydroartemisinin (DHA) on Virally Transformed Lymphoid Cell Lines

Applicants carried out studies to evaluate the in vitro effect of artemisinin (DHA) on two virally transformed lymphoid cell lines. One cell line, referred to as MJ, is an HTLV-I positive cutneous T cell leukemia line and the other cell line, referred to Namalwa, is an EBV positive Burkitt's lymphoma B cell line.

The cell lines were maintained in culture, using RPMI 1640 medium, supplemented with 10% fetal bovine serum and antibiotics. For the assay, 100,000 cells, in volumes of 100 µl medium, were placed in micro-titer wells; an additional 100 µl medium, containing 0 µM, 6.25 µM, 12.5 µM, 25 µM, 50 µM, 100 µM and 200 µM concentrations of DHA, were added. The negative controls contained medium only. The DHA stock (20 mM) was used to dilute the drug in concentrations ranging from 0 to 200 µM. All experiments were performed in triplicate. After incubation at 37° C. and 5% $CO_2$, for various time periods, the cells were counted in a hemocytometer in the presence of trypan blue. Viability was expressed, as % of controls (no drug).

Figure 4:
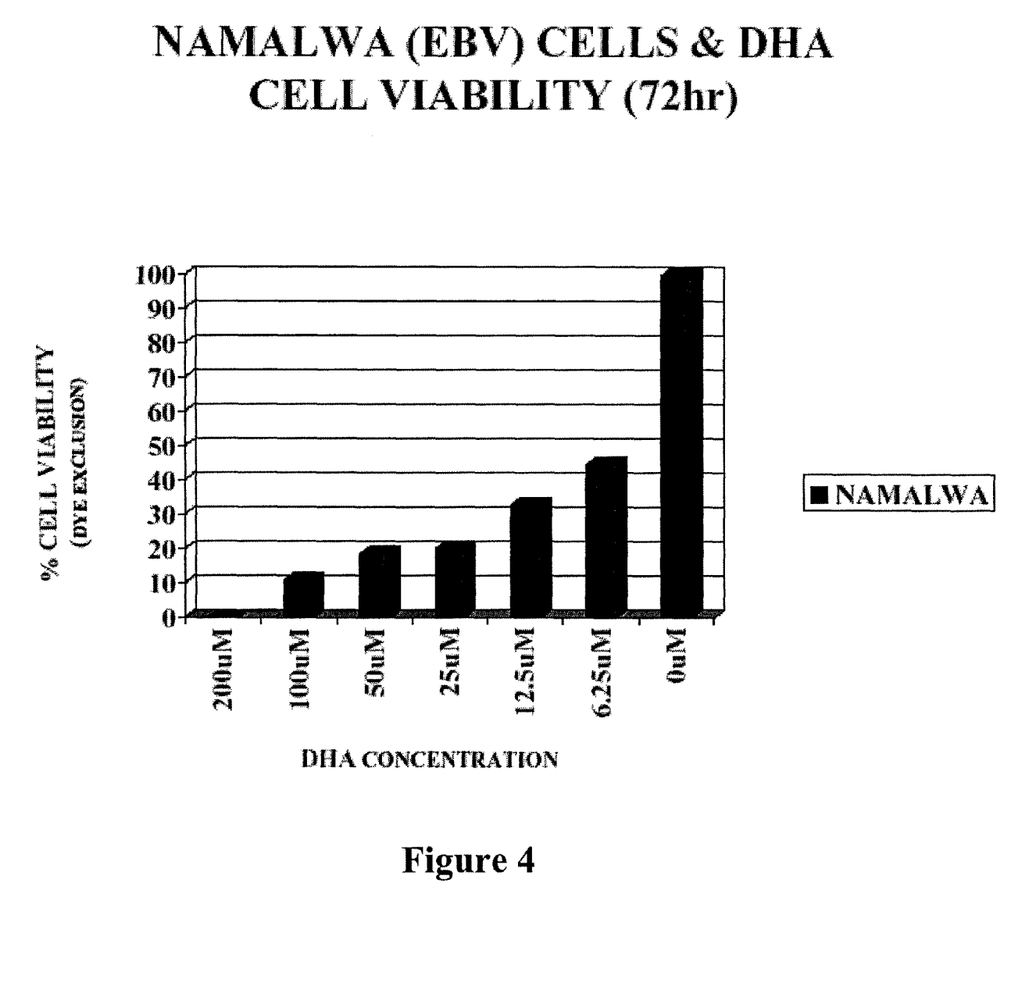
FIG. 4 shows effect of dihydroartemisinin (DHA) on an EBV positive cell line, the Namalwa cell.
Figure 5:
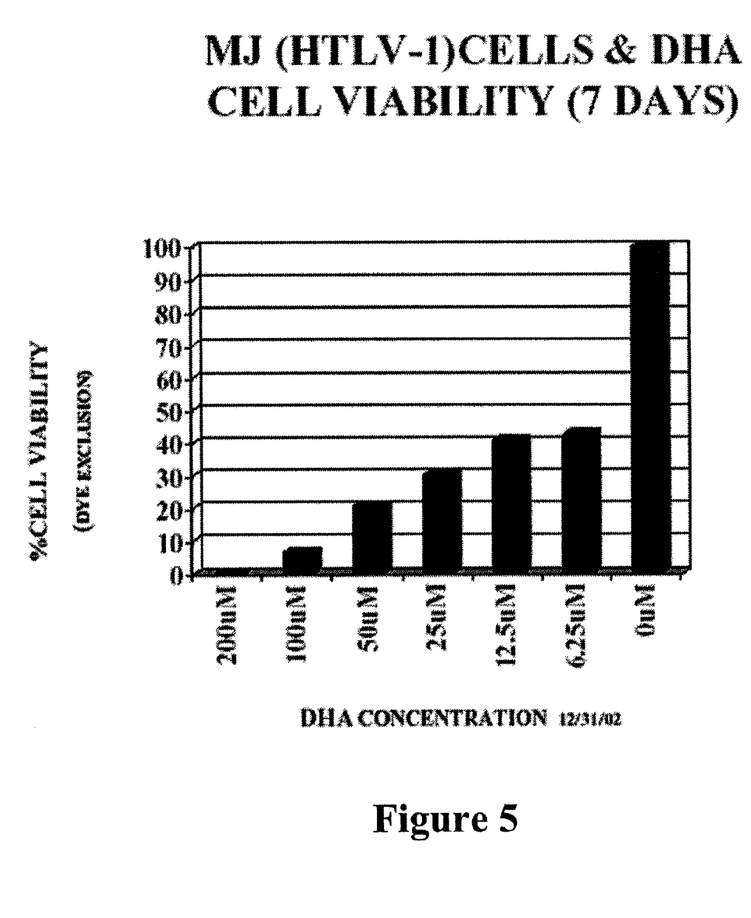
FIG. 5 shows effect of dihydroartemisinin (DHA) on an HTLV-I positive cell line, the MJ cell.

As shown in FIG. 4 and in FIG. 5, DHA killed approximately 60% of both cell types (MJ and Namalwa), at concentrations of 6.25 µM. DHA may kill the transformed cells by interfering with viral mechanisms. Therefore, artemisinin and its analogs (derivatives) may have antiviral activity (including anti-retroviral activity against HTLV and HIV).

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of treating a Human papillomavirus (HPV)-induced condition in a human subject, wherein the condition is selected from the group consisting of oropharyngeal cancer, laryngeal cancer and esophageal cancer, the method comprising:
    identifying a subject with an HPV-postive oropharyngeal cancer, laryngeal cancer or esophageal cancer, and
    administering a therapeutically effective amount of an artemisinin-related compound to the identified subject, wherein the artemisinin-related compound is artemisinin, dihydroartemisinin, artemether, arteether, artesunate, artelinic acid, dihydroartemisinin propyl carbonate, or any combination thereof, and
    wherein the artemisinin-related compound is administered to the identified human subject by oral administration, topical administration, parenteral administration, systemic administration, intramuscular administration, or intravenous administration.

2. The method of claim 1, wherein the artemisinin-related compound is artemisinin.

3. The method of claim 1, wherein the artemisinin-related compound is artesunate.

4. The method of claim 1, wherein the artemisinin-related compound is formulated with a pharmaceutically acceptable carrier.

5. The method of claim 1, wherein the artemisinin-related compound is administered with an anti-viral agent.

6. The method of claim 5, wherein the artemisinin-related compound and the anti-viral agent are in the same formulation.

7. The method of claim 1, wherein the artemisinin-related compound is administered with an anti-cancer agent.

8. The method of claim 7, wherein the artemisinin-related compound and the anti-cancer agent are in the same formulation.

* * * * *